(12) United States Patent
Kasinath et al.

(10) Patent No.: US 11,938,033 B2
(45) Date of Patent: Mar. 26, 2024

(54) INJECTION MOLDED PROSTHETIC COMPONENT WITH PLANARIZED BONE-CONTACTING SURFACES

(71) Applicant: DePuy Synthes Products, Inc., Raynham, MA (US)

(72) Inventors: Rajendra K. Kasinath, Zionsville, IN (US); Jeffrey A. Rybolt, Fort Wayne, IN (US); David A. B. Smith, North Webster, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 879 days.

(21) Appl. No.: 16/917,075

(22) Filed: Jun. 30, 2020

(65) Prior Publication Data
US 2021/0401583 A1 Dec. 30, 2021

(51) Int. Cl.
*A61F 2/30* (2006.01)
*A61F 2/38* (2006.01)
*A61L 27/18* (2006.01)

(52) U.S. Cl.
CPC ........ *A61F 2/3859* (2013.01); *A61F 2/30942* (2013.01); *A61L 27/18* (2013.01); *A61L 2430/02* (2013.01)

(58) Field of Classification Search
CPC ........ A61F 2/30942; A61F 2002/30952; A61F 2002/30957; A61F 2/3859; B29C 2793/009; B29K 2031/7532
See application file for complete search history.

(56) References Cited

U.S. PATENT DOCUMENTS

| | | | |
|---|---|---|---|
| 6,432,349 B1 | 3/2002 | Pletcher | |
| 8,333,805 B2 | 12/2012 | Williams, III et al. | |
| 9,402,747 B2 | 8/2016 | Wogoman | |
| 10,245,148 B2 | 4/2019 | Hanson | |
| 2014/0228860 A1* | 8/2014 | Steines | A61B 34/30 606/130 |
| 2016/0317310 A9 | 11/2016 | Thuliez | |
| 2019/0029833 A1 | 1/2019 | Briscoe et al. | |
| 2019/0167392 A1* | 6/2019 | Faust | A61C 13/0004 |
| 2022/0031433 A1* | 2/2022 | Diez | A61C 13/0004 |

FOREIGN PATENT DOCUMENTS

| | | | |
|---|---|---|---|
| EP | 1321113 A2 | 6/2003 | |
| WO | WO-2020057872 A1 * | 3/2020 | A61C 13/0004 |

OTHER PUBLICATIONS

Machine translation of Diez et al (WO 2020/057872 A1) dated Mar. 26, 2020. (Year: 2020).*

(Continued)

*Primary Examiner* — Robert B Davis
(74) *Attorney, Agent, or Firm* — Barnes & Thornburg LLP (57) ABSTRACT

A method for manufacturing a prosthetic component include injection molding a prosthetic component with a polymeric material. The prosthetic component includes a final surface positioned on one side and multiple coring features positioned on an opposite side. The coring features may include multiple ribs and slots. The method further includes machining the prosthetic component to remove the coring features and form a final surface on the opposite side. The prosthetic component may be a femoral component for a prosthetic knee joint.

11 Claims, 5 Drawing Sheets

(56) References Cited

OTHER PUBLICATIONS

International Search report. International Application No. PCT/IB2021054799, dated Aug. 9, 2021. 7 pages.
Solvay: "Speciality Polymers Ketaspire PEEK Design & Processing Guide", Jan. 1, 2014 (Jan. 1, 2014). pp. 1-126, XP055828643, Retrieved from the internet: URL: https://www.nevicolor.it/prodotti/ricerca-polimero/solvay/ketaspire-peek-drink/documenti/ketaspire-peek-manuale-design-processing-guide.pdf [retrieved on Aug. 18, 2021].

* cited by examiner

INJECTION MOLDED PROSTHETIC COMPONENT WITH PLANARIZED BONE-CONTACTING SURFACES

TECHNICAL FIELD

The present disclosure relates generally to an implantable orthopaedic knee prosthesis, and more particularly to an implantable femoral component of an orthopaedic knee prosthesis.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. A typical knee prosthesis includes a tibial tray, a femoral component, and a polymer insert or bearing positioned between the tibial tray and the femoral component. The tibial tray generally includes a plate having a stem extending distally therefrom, and the femoral component generally includes a pair of spaced apart condylar elements, which include surfaces that articulate with corresponding surfaces of the polymer bearing. The stem of the tibial tray is configured to be implanted in a surgically-prepared medullary canal of the patient's tibia, and the femoral component is configured to be coupled to a surgically-prepared distal end of a patient's femur.

SUMMARY

According to one aspect of the disclosure, a prosthetic component includes a unitary body formed from a polymeric material. The unitary body includes a first surface positioned on a first side of the unitary body, wherein the first side comprises one of a bearing side or a bone-facing side, a back surface positioned on a second side of the unitary body opposite the first surface, and a plurality of coring features positioned on the second side of the unitary body and extending from the back surface. Each of the coring features has a wall thickness greater than a reference thickness, and the reference thickness is less than or equal to a distance between the first surface and the back surface.

In an embodiment, the polymeric material comprises a polyether ether ketone (PEEK) polymer. In an embodiment, the polymeric material has a melt flow index that is at least about 10 g/10 min.

In an embodiment, the plurality of coring features include a plurality of ribs separated by a plurality of slots, wherein each rib extends outwardly from the back surface toward an outer surface of the rib, wherein the outer surface of each rib is positioned on the second side of the prosthetic component. In an embodiment, the back surface at each slot is spaced apart from the first surface by at least the reference thickness.

In an embodiment, the first surface is a bearing surface, the first side is the bearing side, and the second side is the bone-facing side. In an embodiment, the prosthetic component further includes a datum coupled to the prosthetic component, wherein the datum comprises a planar surface at a predetermined position and orientation relative to the prosthetic component.

In an embodiment, the first surface is a bone-contacting surface, the first side is the bone-facing side, and the second side is the bearing side.

In an embodiment, the prosthetic component includes a femoral component for a knee prosthesis.

According to another aspect, a method for prosthetic component manufacturing includes injection molding a prosthetic component with a polymeric material, wherein the prosthetic component includes a first side and a second side positioned opposite the first side, wherein the prosthetic component further includes a first surface positioned on the first side, and wherein the prosthetic component further includes a plurality of coring features positioned on the second side; and machining the prosthetic component to remove the coring features, wherein the prosthetic component after machining includes a second surface positioned on the second side.

In an embodiment, each of the plurality of coring features has a wall thickness greater than a reference thickness, and wherein the prosthetic component after machining has the reference thickness between the first surface and the second surface.

In an embodiment, the plurality of coring features includes a plurality of ribs separated by a plurality of slots, wherein each rib extends outwardly from a back surface of a the prosthetic component toward an outer surface of the rib, wherein the outer surface of each rib is positioned on the second side of the prosthetic component. In an embodiment, machining the prosthetic component includes forming the second surface by removing the plurality of ribs.

In an embodiment, the prosthetic component is a femoral component for a knee prosthesis.

In an embodiment, the first surface is a bearing surface, and the second surface is a bone-contacting surface. In an embodiment, the bone-contacting surface includes a plurality of planar facets. In an embodiment, the method further includes coating each of the plurality of planar facets with a porous coating. In an embodiment, the prosthetic component is a femoral component for a knee prosthesis, and the plurality of planar facets includes an anterior femur facet, an anterior chamfer facet, a distal femur facet, a posterior chamfer facet, and a posterior femur facet.

In an embodiment, the method further includes removing a datum from the prosthetic component in response to machining the prosthetic component, wherein the datum comprises a planar surface at a predetermined position and orientation relative to the prosthetic component; wherein injection molding the prosthetic component includes forming the datum of the prosthetic component; and wherein machining the prosthetic component includes registering the datum.

In an embodiment, machining the prosthetic component to remove the coring features includes forming a mounting feature that extends from the second surface after machining.

According to another aspect, a prosthetic component is manufactured by method comprising injection molding a prosthetic component with a polymeric material, wherein the prosthetic component includes a first side and a second side positioned opposite the first side, wherein the prosthetic component further includes a first surface positioned on the first side, and wherein the prosthetic component further includes a plurality of coring features positioned on the second side; and machining the prosthetic component to remove the coring features, wherein the prosthetic component after machining includes a second surface positioned on the second side. In an embodiment, the polymeric material comprises a polyether ether ketone (PEEK) polymer. In an embodiment, the polymeric material has a melt flow index that is at least about 10 g/10 min.

In an embodiment, each of the plurality of coring features has a wall thickness greater than a reference thickness, and wherein the prosthetic component after machining has the reference thickness between the first surface and the second surface.

In an embodiment, the plurality of coring features includes a plurality of ribs separated by a plurality of slots, wherein each rib extends outwardly from a back surface of a the prosthetic component toward an outer surface of the rib, wherein the outer surface of each rib is positioned on the second side of the prosthetic component. In an embodiment, machining the prosthetic component includes forming the second surface by removing the plurality of ribs.

In an embodiment, the prosthetic component is a femoral component for a knee prosthesis.

In an embodiment, the first surface is a bearing surface, and the second surface is a bone-contacting surface. In an embodiment, the bone-contacting surface includes a plurality of planar facets. In an embodiment, the method further includes coating each of the plurality of planar facets with a porous coating. In an embodiment, the prosthetic component is a femoral component for a knee prosthesis, and the plurality of planar facets includes an anterior femur facet, an anterior chamfer facet, a distal femur facet, a posterior chamfer facet, and a posterior femur facet.

In an embodiment, the method further includes removing a datum from the prosthetic component in response to machining the prosthetic component, wherein the datum comprises a planar surface at a predetermined position and orientation relative to the prosthetic component; wherein injection molding the prosthetic component includes forming the datum of the prosthetic component; and wherein machining the prosthetic component includes registering the datum.

In an embodiment, the first surface is a bone-contacting surface, the first side is the bone-facing side, and the second side is the bearing side.

In an embodiment, machining the prosthetic component to remove the coring features includes forming a mounting feature that extends from the second surface after machining.

BRIEF DESCRIPTION OF THE DRAWINGS

The detailed description particularly refers to the following figures, in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and orthopaedic surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Figure 1:
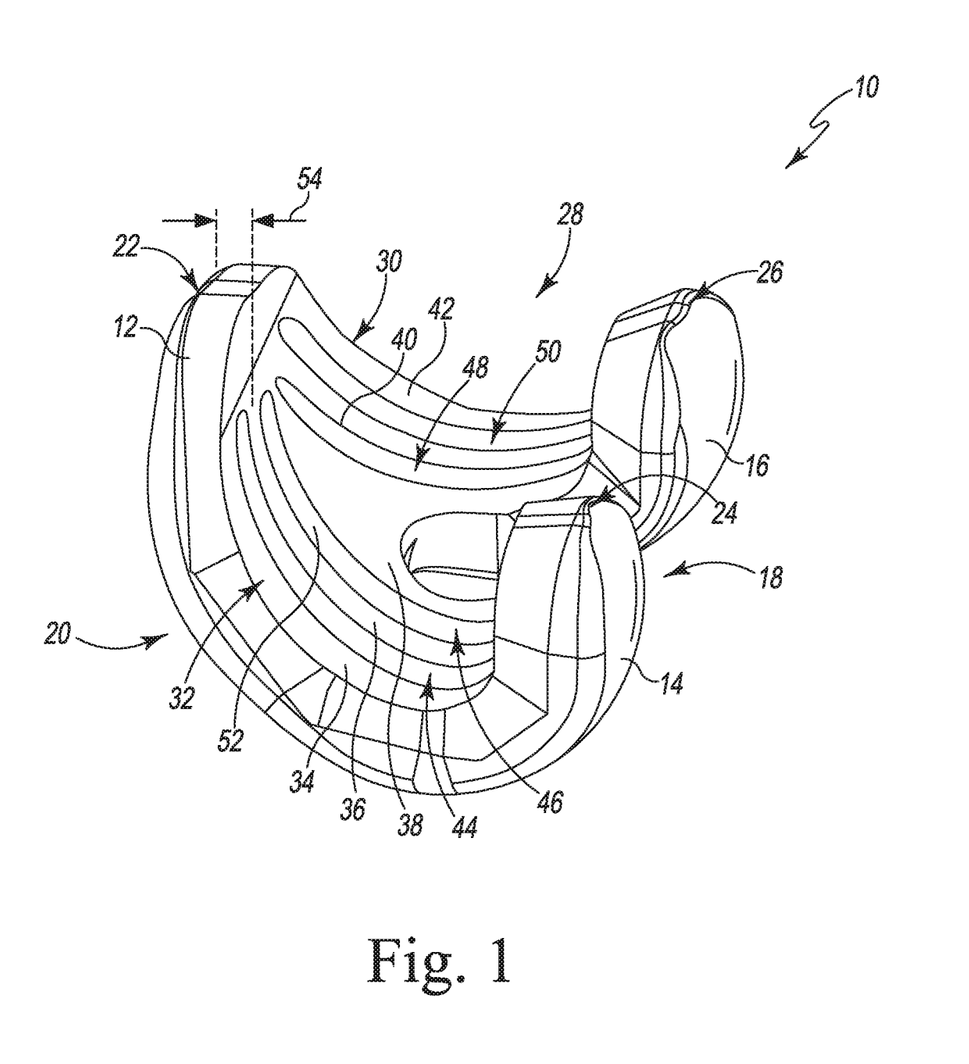
FIG. 1 is a perspective view of a femoral component of a knee prosthesis produced by an injection molding process.
Figure 2:
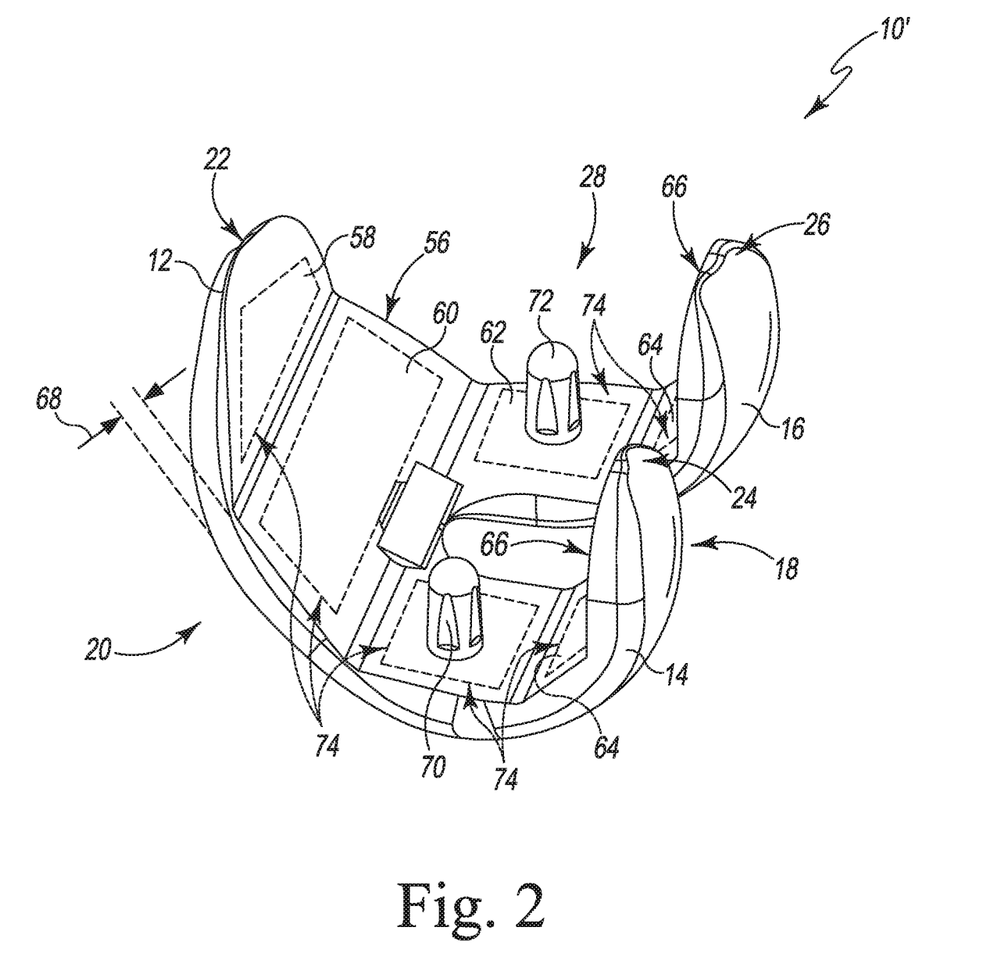
FIG. 2 is a perspective view of the femoral component of FIG. 1 following a machining process.

Referring now to FIGS. 1-2, an illustrative embodiment of a femoral component 10 provided in accordance with the present disclosure is shown. It should be understood that the femoral component 10 may be included in an orthopaedic system with other orthopaedic components, such as a tibial tray and a tibial insert. The illustrative femoral component 10 includes a unitary body formed from a polymeric material, such as a polyether ether ketone (PEEK) polymer, Ultem®/polyetherimide (PEI), polyacetal, a PEEK blend (for example including PEI, polyphenylsulfone (PPSU), etc.), or other thermoplastic that is amenable to conventional machining. The femoral component may be formed using an injection molding process.

The femoral component 10 includes an anterior flange 12 and a pair of condyles 14, 16 extending posteriorly from the anterior flange 12. An intercondylar notch 18 is defined between the pair of condyles 14, 16. The femoral component 10 includes an outer, articulating surface 20 extending from an anterior end 22 of the anterior flange 12 to respective posterior ends 24, 26 of the condyles 14, 16. In use, the condyles 14, 16 replace the natural condyles of the patient's femur, and the articulating surface 20 is configured to articulate on corresponding bearing surfaces of the tibial bearing (not shown).

The prosthetic component 10 includes a bone-facing side 28 positioned opposite the articulating surface 20. Referring now to FIG. 1, the prosthetic component 10 as produced by the injection molding process is shown. As shown in FIG. 1, the bone-facing side 28 includes an outer surface 30. Multiple coring features 32 are defined in the outer surface 30. Injection molding processes typically require that molded components have near-constant or otherwise uniform wall thickness to ensure dimensional stability in as-finished components. The coring features 32 may include ribs, slots, voids, cutouts, or other features defined in the outer surface 30 that enable dimensional stability of the femoral component 10.

Illustratively, the coring features 32 include multiple ribs 34, 36, 38, 40, 42 extending from the anterior flange 12 to the condyles 14, 16. The ribs 34, 36, 38, 40, 42 are separated by slots 44, 46, 48, 50 defined in the outer surface 30. Each slot 44, 46, 48, 50 extends inwardly from the outer surface 30 to a back surface 52. The back surface 52 may be separated from the articulating surface 20 by a wall thickness 54. The thickness 54 may be similar to a wall thickness of the ribs 34, 36, 38, 40, 42. Although illustrated as multiple ribs and slots, it should be understood that in other embodiments the femoral component 10 may include a different number and/or arrangement of coring features 32.

Referring now to FIG. 2, the femoral component 10' is shown after undergoing a machining process to remove the coring features 32. The femoral component 10 may be machined using a 4-axis machining process, a 5-axis machining process, or other machining process that cuts, mills, or otherwise removes material from the femoral component 10. In some embodiments, the machining process may register one or more datums or other predetermined locations on the femoral component 10 (not shown).

As shown in FIG. 2, after removal of the coring features 32, the back side 28 of the femoral component 10' includes a bone-contacting surface 56. The illustrative bone-contacting surface 56 includes multiple planar surfaces 58, 60, 62, 64, 66. Each of the planar surfaces 58, 60, 62, 64, 66 is configured to be attached to a corresponding surface of a surgically-prepared distal end of a patient's femur. For example, the illustrative planar surfaces 58, 60, 62, 64, 66 correspond to the anterior femur, anterior chamfer, distal femur, posterior chamfer, and posterior femur, respectively.

The bone-contacting surface 56 is separated from the articulating surface 20 by a wall thickness 68, which may be a maximum thickness, uniform thickness, or other measure of wall thickness. In some embodiments, parts of the bone-contacting surface 56 may coincide with the back surface 52 of the coring features 32. In those embodiments, the thicknesses 54, 68 may be the same. Additionally or alternatively, in some embodiments, part or all of the back surface 52 of the coring features 32 may be removed during the machining process. In those embodiments, the thickness 68 may be thinner than the thickness 54.

The femoral component 10' further includes a pair of lugs 70, 72 extending outwardly from the bone-contacting surface 56. The lugs 70, 72 are formed during the machining process out of the coring features 32. The lugs 70, 72 are configured to be inserted in corresponding lug holes drilled in the surgically-prepared distal end of the patient's femur. It should be understood that in some embodiments, the femoral component 10' may include a different number and/or arrangement of lugs or other mounting features.

In some embodiments, the bone-contacting surface 56 may include a porous coating 74 on one or more of the planar surfaces 58, 60, 62, 64, 66. The porous coating 74 is configured to promote bone growth and support fixation of the femoral component 10' in the patient's bone.

As shown in FIG. 2, the femoral component 10' includes the articulating surface 20 positioned opposite the bone-contacting surface 56. Accordingly, in the illustrative embodiment, the machining process does not alter the articulating surface 20. Thus, in the illustrative embodiment, the articulating surface 20 is in its final configuration after the injection molding process.

In an illustrative embodiment, a method for manufacturing the femoral component 10 in accordance with the present disclosure includes injection molding the femoral component 10 from a polymeric material as shown in FIG. 1, including the coring features 32. The method further includes machining the femoral component 10 to remove the coring features 32 and to form the femoral component 10' as shown in FIG. 2, including the bone-contacting surface 56 having multiple planar surfaces. In some embodiments, the method may further include coating the planar surfaces with the porous coating 74 to promote bone ingrowth. The planar surfaces may be coated with the porous coating 74 using any appropriate process.

Accordingly, the methods disclosed herein may enable cost-effective manufacturing of polymeric orthopaedic implants using injection molding and post-molding machining processes. The orthopaedic implants produced as described herein (e.g., the femoral component 10', 100') have complex geometry, including planar surfaces that are suitable for porous coating. Accordingly, orthopaedic implants produced as described herein may be suitable for cementless application.

After manufacturing using the injection molding and machining process described above, the femoral component 10' may have a higher melt flow index (MFI) as compared to components manufactured using a different process. Melt flow index is a measure of the ease of flow of the melt of a thermoplastic polymer, and is expressed as the number of grams of polymer melt that flows through a standardized opening under defined test conditions in ten minutes (g/10 min). In particular, the MFI for the femoral component 10' may be on the order of 5-10 times higher than the MFI of a component machined from extruded polymer (e.g., machined from bar stock). As an illustrative example, the MFI for the femoral component 10' may be at least 10 g/10 min.

Additionally, the femoral component 10' may have a different microscopic structure as compared to components manufactured using a different process. As described above, the femoral component 10' is formed from a polymeric material, which is semicrystalline. X-ray diffraction (XRD) may be used to determine the crystalline structure of the femoral component 10', and in particular to determine a pattern of peaks and associated intensities caused by the internal structure of the femoral component 10'. This XRD pattern associated with the femoral component 10', which is formed using the injection molding and machining process described above, is expected to be different from an XRD pattern of a component machined from extruded polymer.

In some embodiments, the femoral component 10' may have different mechanical properties such as strength, modulus, and isotropy as compared to components manufactured using a different process. For example, the femoral component 10' may include a filler material such as carbon fiber, glass fiber, or other reinforcing fibers. In those embodiments, the mold may be configured to manipulate shear of the material to orient fibers during the injection molding process. Due to the orientation of those fibers, the femoral component 10' may have different mechanical properties in different directions (i.e., anisotropic mechanical properties), and may have different mechanical properties as compared to materials with randomly oriented fibers. For example, a femoral component 10' with fibers oriented during injection molding may have anisotropic strength, modulus, or other properties, as compared to a component machined from an unfilled material or a material with randomly oriented fibers, which has the same mechanical properties in all directions.

Figure 3:
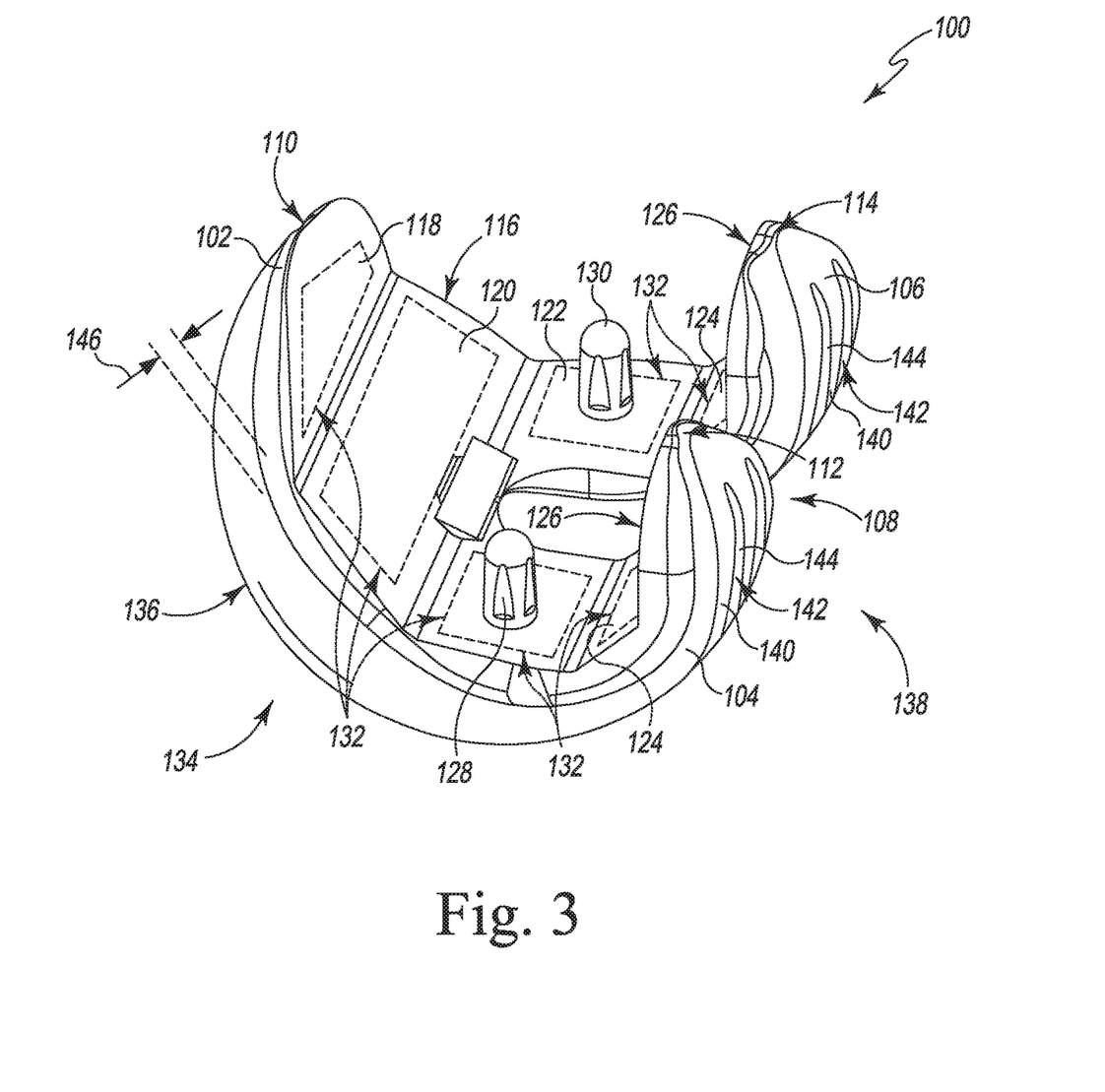
FIG. 3 is a perspective view of another femoral component of a knee prosthesis produced by an injection molding process.
Figure 4:
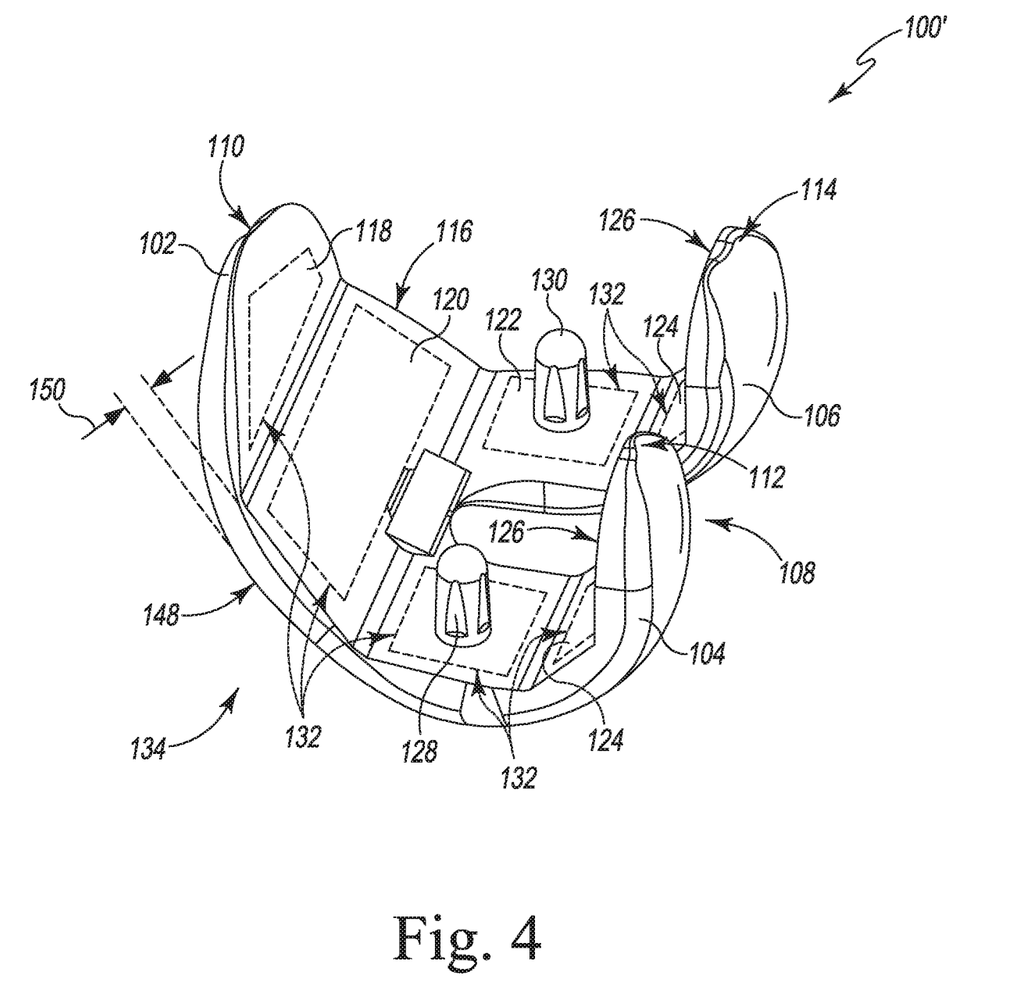
FIG. 4 is a perspective view of the femoral component of FIG. 3 following a machining process.

Referring now to FIGS. 3-4, another illustrative embodiment of a femoral component 100 provided in accordance with the present disclosure is shown. It should be understood that the femoral component 100 may be included in an orthopaedic system with other orthopaedic components, such as a tibial tray and a tibial insert. Similar to the femoral component 10, the illustrative femoral component 100 includes a unitary body formed from a polymeric material, such as a polyether ether ketone (PEEK) polymer, Ultem®/ polyetherimide (PEI), polyacetal, a PEEK blend (for example including PEI, polyphenylsulfone (PPSU), etc.), or other thermoplastic that is amenable to conventional machining. The femoral component may be formed using an injection molding process.

The femoral component 100 includes an anterior flange 102 and a pair of condyles 104, 106 extending posteriorly from the anterior flange 102. An intercondylar notch 108 is defined between the pair of condyles 104, 106. The femoral component 100 includes a bone-contacting surface 116 that extends from an anterior end 110 of the anterior flange 102 to respective posterior ends 112, 114 of the condyles 104, 106. The illustrative bone-contacting surface 116 includes multiple planar surfaces 118, 120, 122, 124, 126. Each of the planar surfaces 118, 120, 122, 124, 126 is configured to be attached to a corresponding surface of a surgically-prepared distal end of a patient's femur. For example, the illustrative planar surfaces 118, 120, 122, 124, 126 correspond to the anterior femur, anterior chamfer, distal femur, posterior chamfer, and posterior femur, respectively.

The femoral component 100 further includes a pair of lugs 128, 130 extending outwardly from the bone-contacting surface 116. The lugs 128, 130 are formed during the injection molding process. The lugs 128, 130 are configured to be inserted in corresponding lug holes drilled in the surgically-prepared distal end of the patient's femur. It should be understood that in some embodiments, the femoral component 100 may include a different number and/or arrangement of lugs or other mounting features.

In some embodiments, the bone-contacting surface 116 may include a porous coating 132 on one or more of the planar surfaces 118, 120, 122, 124, 126. The porous coating 132 is configured to promote bone growth and support fixation of the femoral component 100 in the patient's bone.

The prosthetic component 100 includes a bearing side 134 positioned opposite the bone-contacting surface 116. Referring now to FIG. 1, the prosthetic component 100 as produced by the injection molding process is shown. As shown in FIG. 1, the bearing side 134 includes an outer surface 136. Multiple coring features 138 are defined in the outer surface 136. As described above, injection molding processes typically require that molded components have near-constant or otherwise uniform wall thickness to ensure dimensional stability in as-finished components. The coring features 138 may include ribs, voids, cutouts, or other features defined in the outer surface 136 that enable dimensional stability of the femoral component 100.

Illustratively, the coring features 138 include multiple ribs 140 extending from the anterior flange 12 to the condyles 14, 16. The ribs 140 are separated by slots 142 defined in the outer surface 136. Each slot 142 extends inwardly from the outer surface 136 to a back surface 144. The back surface 144 may be separated from the bone-contacting surface 116 by a wall thickness 146. The thickness 146 may be similar to a wall thickness of the ribs 140. Although illustrated as multiple ribs 140 and slots 142, it should be understood that in other embodiments the femoral component 100 may include a different number and/or arrangement of coring features 138.

Referring now to FIG. 4, the femoral component 100 is shown after undergoing a machining process to remove the coring features 138 as femoral component 100'. The femoral component 100 may be machined using a 4-axis machining process, a 5-axis machining process, or other machining process that cuts, mills, or otherwise removes material from the femoral component 100. In some embodiments, the machining process may register one or more of the planar surfaces 118, 120, 122, 124, 126, datums, or other predetermined locations on the femoral component 100.

As shown in FIG. 4, after removal of the coring features 138, the bearing side 134 of the femoral component 100' includes an articulating surface 148. In use, the condyles 104, 106 replace the natural condyles of the patient's femur, and the articulating surface 148 is configured to articulate on corresponding bearing surfaces of the tibial bearing (not shown). The bone-contacting surface 116 is separated from the articulating surface 148 by a wall thickness 150, which may be a maximum thickness, uniform thickness, or other measure of wall thickness. In some embodiments, parts of the articulating surface 148 may coincide with the back surface 144 of the coring features 138. In those embodiments, the thicknesses 146, 150 may be the same. Additionally or alternatively, in some embodiments, part or all of the back surface 144 of the coring features 138 may be removed during the machining process. In those embodiments, the thickness 150 may be thinner than the thickness 146.

As shown in FIG. 4, the femoral component 100' includes the bone-contacting surface 116 positioned opposite the articulating surface 148. Accordingly, in the illustrative embodiment, the machining process does not alter the bone-facing surface 116. Thus, in the illustrative embodiment, the bone-facing surface 116 is in its final configuration after the injection molding process.

In an illustrative embodiment, a method for manufacturing the femoral component 100 in accordance with the present disclosure includes injection molding the femoral component 100 from a polymeric material as shown in FIG. 3, including the coring features 138. The method further includes machining the femoral component 100 to remove the coring features 138 and to form the femoral component 100' as shown in FIG. 4, including the articulating surface 148. In some embodiments, the method may further include coating the planar surfaces 118, 120, 122, 124, 126 with the porous coating 132 to promote bone ingrowth. The planar surfaces may be coated with the porous coating 132 using any appropriate process.

Figure 5:
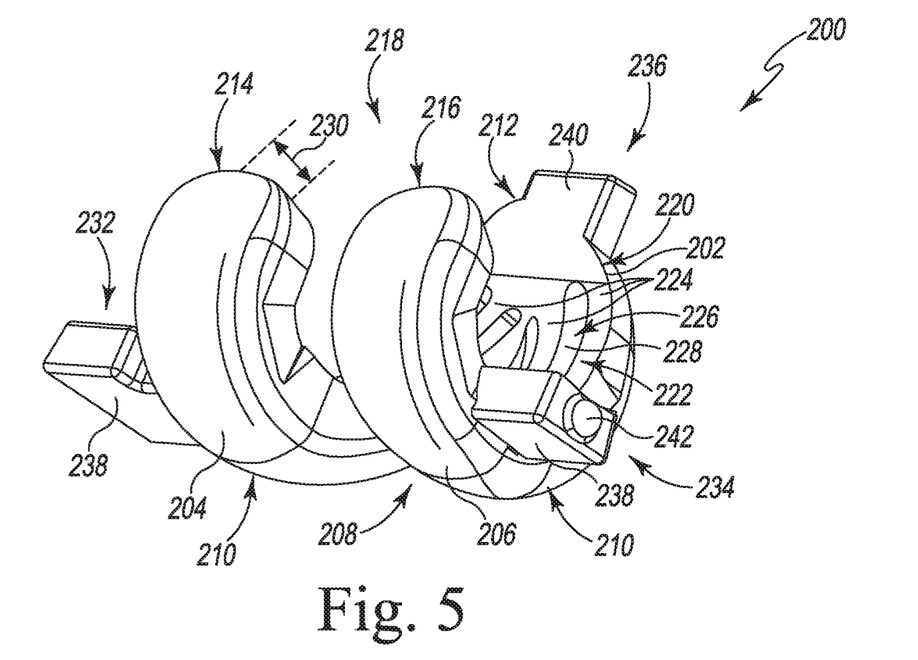
FIGS. 5 and 6 are perspective views of another femoral component of a knee prosthesis produced by an injection molding process.
Figure 6:
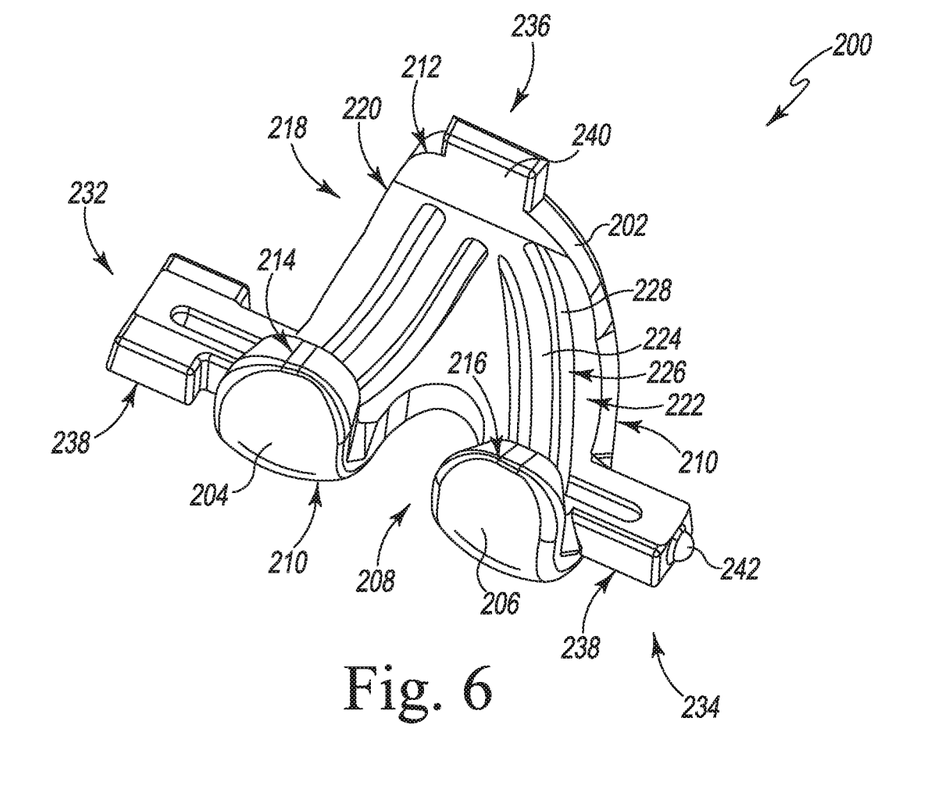

Referring now to FIGS. 5 and 6, another illustrative embodiment of a femoral component 200 provided in according with the present disclosure is shown. It should be understood that the femoral component 200 may be included in an orthopaedic system with other orthopaedic components, such as a tibial tray and a tibial insert. The illustrative femoral component 200 includes a unitary body formed from a polymeric material, such as a polyether ether ketone (PEEK) polymer, Ultem®/polyetherimide (PEI), polyacetal, a PEEK blend (for example including PEI, polyphenylsulfone (PPSU), etc.), or other thermoplastic that is amenable to conventional machining. The femoral component may be formed using an injection molding process.

The femoral component 200 includes an anterior flange 202 and a pair of condyles 204, 206 extending posteriorly from the anterior flange 202. An intercondylar notch 208 is defined between the pair of condyles 204, 206. The femoral component 200 includes an outer, articulating surface 210 extending from an anterior end 212 of the anterior flange 202 to respective posterior ends 214, 216 of the condyles 204, 206. In use, the condyles 204, 206 replace the natural condyles of the patient's femur, and the articulating surface 210 is configured to articulate on corresponding bearing surfaces of the tibial bearing (not shown).

The prosthetic component 10 includes a bone-facing side 218 positioned opposite the articulating surface 210. As shown in FIG. 5, the bone-facing side 218 of the prosthetic component 200 as produced by the injection molding process includes an outer surface 220. Multiple coring features 222 are defined in the outer surface 220. As described above, injection molding processes typically require that molded components have near-constant or otherwise uniform wall thickness to ensure dimensional stability in as-finished components. The coring features 222 may include ribs, voids, cutouts, or other features defined in the outer surface 220 that enable dimensional stability of the femoral component 200.

Illustratively, the coring features 222 include multiple ribs 224 extending from the anterior flange 202 to the condyles 204, 206. The ribs 224 are separated by slots 226 defined in the outer surface 220. Each slot 226 extends inwardly from the outer surface 220 to a back surface 228. The back surface 228 may be separated from the articulating surface 210 by a wall thickness 230. The thickness 230 may be similar to a wall thickness of the ribs 224. Although illustrated as multiple ribs 224 and slots 226, it should be understood that in other embodiments the femoral component 200 may include a different number and/or arrangement of coring features 222.

As shown in FIGS. 5 and 6, the illustrative femoral component 200 includes multiple datums 232, 234, 236. Each datum 232, 234, 236 includes one or more planar sides or other features that may be registered by a machining process. Illustratively, the datums 232, 234 each include a co-planar registering surface 238. The datum 236 includes a registering surface 240. The illustrative registering surfaces 238, 240 are planar and not parallel; in other words, each of the registering surfaces 238, 240 define respective intersecting imaginary planes. The datum 234 further includes a semihemispherical registering feature 242. As described above, the machining process may register the registering surfaces 238, 240, 242 of the datums 232, 234, 236 of the femoral component 200.

In an illustrative embodiment, a method for manufacturing the femoral component 200 in accordance with the present disclosure includes injection molding the femoral component 200 from a polymeric material as shown in FIGS. 5 and 6, including the coring features 222. The method further includes machining the femoral component 200 to remove the coring features 222. As described above, during the machining process, the datums 232, 234, 236 are registered in order for the machining process to determine the position and/or orientation of the femoral component 200. After the coring features 222 are removed, the datums 232, 234, 236 are also removed. The resulting machined femoral component may be similar to and/or the same as the femoral component 10' as shown in FIG. 2, including the bone-contacting surface 56 having multiple planar surfaces. In some embodiments, the method may further include coating the planar surfaces with the porous coating 74 to promote bone ingrowth. The planar surfaces may be coated with the porous coating 74 using any appropriate process.

Additionally or alternatively, although illustrated as manufacturing prosthetic femoral components 10, 100, 200 it should be understood that the techniques of the present disclosure may apply to other prosthetic components or prosthetic systems, including tibial tray components, tibial inserts, components for prosthetic hip replacements (e.g., acetabular components, femoral head components, etc.), or other prosthetic components.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A method for prosthetic component manufacturing, the method comprising:
   injection molding a prosthetic component with a polymeric material, wherein the prosthetic component includes a first side and a second side positioned opposite the first side, wherein the prosthetic component further includes a first surface positioned on the first side, and wherein the prosthetic component further includes a plurality of coring features positioned on the second side, the coring features comprising a portion of the prosthetic component that provides dimensional stability; and
   machining the prosthetic component to remove the coring features, wherein the prosthetic component after machining includes a second surface positioned on the second side.

2. The method of claim 1, wherein each of the plurality of coring features has a wall thickness greater than a reference thickness, and wherein the prosthetic component after machining has the reference thickness between the first surface and the second surface.

3. A method for prosthetic component manufacturing, the method comprising:
   injection molding a prosthetic component with a polymeric material, wherein the prosthetic component includes a first side and a second side positioned opposite the first side, wherein the prosthetic component further includes a first surface positioned on the first side, and wherein the prosthetic component further includes a plurality of coring features positioned on the second side; and
   machining the prosthetic component to remove the coring features, wherein the prosthetic component after machining includes a second surface positioned on the second side;
   wherein the plurality of coring features comprises a plurality of ribs separated by a plurality of slots, wherein each rib extends outwardly from a back surface of the prosthetic component toward an outer surface of the rib, wherein the outer surface of each rib is positioned on the second side of the prosthetic component.

4. The method of claim 3, wherein machining the prosthetic component comprises forming the second surface by removing the plurality of ribs.

5. The method of claim 1, wherein the prosthetic component comprises a femoral component for a knee prosthesis.

6. The method of claim 1, wherein the first surface comprises a bearing surface, and the second surface comprises a bone-contacting surface.

7. The method of claim 6, wherein the bone-contacting surface comprises a plurality of planar facets.

8. The method of claim 7, further comprising coating each of the plurality of planar facets with a porous coating.

9. The method of claim 7, wherein:
   the prosthetic component comprises a femoral component for a knee prosthesis; and
   the plurality of planar facets comprises an anterior femur facet, an anterior chamfer facet, a distal femur facet, a posterior chamfer facet, and a posterior femur facet.

10. The method of claim 6, further comprising:
- removing a datum from the prosthetic component after machining the prosthetic component, wherein the datum comprises a planar surface at a predetermined position and orientation relative to the prosthetic component;
- wherein injection molding the prosthetic component comprises forming the datum of the prosthetic component; and
- wherein machining the prosthetic component comprises registering the datum.

11. The method of claim 1, wherein machining the prosthetic component to remove the coring features comprises forming a mounting feature that extends from the second surface after machining.

* * * * *